US010449315B2

(12) United States Patent
Hitchcock et al.

(10) Patent No.: US 10,449,315 B2
(45) Date of Patent: Oct. 22, 2019

(54) RESPIRATORY MASKS WITH GUSSETED CUSHIONS

(71) Applicant: ResMed Pty Ltd, Bella Vista, New South Wales (AU)

(72) Inventors: Robin Garth Hitchcock, Sydney (AU); Aaron Samuel Davidson, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 15/063,825

(22) Filed: Mar. 8, 2016

(65) Prior Publication Data
US 2016/0206843 A1 Jul. 21, 2016

Related U.S. Application Data

(63) Continuation of application No. 13/654,600, filed on Oct. 18, 2012, now Pat. No. 9,308,342, which is a (Continued)

(51) Int. Cl.
*A61M 16/06* (2006.01)
*A61M 16/08* (2006.01)

(52) U.S. Cl.
CPC ........ *A61M 16/0611* (2014.02); *A61M 16/06* (2013.01); *A61M 16/0616* (2014.02);
(Continued)

(58) Field of Classification Search
CPC .......... A61M 15/0043; A61M 15/0045; A61M 15/0051; A61M 15/0055; A61M 15/0065;
(Continued)

(56) References Cited

U.S. PATENT DOCUMENTS

| | | | |
|---|---|---|---|
| 2,130,555 | A | 9/1938 | Malcom |
| 2,133,699 | A | 10/1938 | Heidbrink |

(Continued)

FOREIGN PATENT DOCUMENTS

| | | |
|---|---|---|
| DE | 4 233 448 | 4/1993 |
| DE | 196 03 949 | 8/1997 |

(Continued)

OTHER PUBLICATIONS

First Examination Report issued in corresponding New Zealand Application No. 722620 dated Aug. 18, 2016.
(Continued)

*Primary Examiner* — Annette Dixon
(74) *Attorney, Agent, or Firm* — Nixon & Vanderhye P.C.

(57) ABSTRACT

A respiratory mask assembly for treatment of sleep disordered breathing includes a frame, a cushion which at least in part defines a cavity adapted to receive at least a patient's nose, and an air delivery connection supported by the frame and adapted to connect an air delivery conduit to supply air to the cavity. The cushion includes a face contacting portion, a non-face contacting portion, and a gusset portion between the face contacting portion and the non-face contacting portion. The gusset portion includes a hanging portion that, when seen in cross-section, hangs over an adjacent exterior surface of the cushion. The gusset portion includes a first point adjacent to the face contacting portion and a second point adjacent to the non-face contacting portion, and the first point is offset radially outwardly from the second point.

23 Claims, 17 Drawing Sheets

Related U.S. Application Data continuation of application No. 11/793,051, filed as application No. PCT/AU2006/000034 on Jan. 12, 2006, now Pat. No. 8,297,283.

(60) Provisional application No. 60/643,115, filed on Jan. 12, 2005.

(52) U.S. Cl.
CPC .... *A61M 16/0622* (2014.02); *A61M 16/0633* (2014.02); *A61M 16/0683* (2013.01); *A61M 16/0816* (2013.01); *A61M 16/0858* (2014.02)

(58) Field of Classification Search
CPC .............. A61M 16/00; A61M 16/0075; A61M 16/0084; A61M 16/06; A61M 16/0611; A61M 16/0616; A61M 16/0622; A61M 16/0633; A61M 16/0638; A61M 16/0666; A61M 16/0683; A61M 16/08; A61M 16/0816; A61M 16/0825; A61M 16/16; A61M 2016/0611; A61M 2016/0616; A61M 2016/0622; A61M 2016/0633; A61M 2016/0638; A61M 2016/0661; A61M 2016/0825; A61M 2202/064; A61M 2205/0233; A61M 2206/14; A61M 2209/06; A63C 11/00; A62B 17/04; A62B 18/00; A62B 18/02; A62B 18/025; A62B 18/08; A62B 18/084; A62B 21/00; A62B 23/00; A62B 23/02; A62B 7/00; A62B 7/04; A62B 9/00; A62B 9/02; A62B 9/022; A62B 9/04; B29C 67/00; B63C 11/02; B63C 11/12; B63C 11/14; B63C 11/22; B64D 10/00
USPC ............ 128/200.24, 200.29, 201.19, 201.24, 128/204.18, 204.27, 205.13, 205.18, 128/205.25, 206.12, 206.17, 206.18, 128/206.21, 206.23, 206.24, 206.25, 128/206.26, 206.27, 206.28, 207.11, 128/207.13, 857, 863

See application file for complete search history.

(56) References Cited

U.S. PATENT DOCUMENTS

| | | |
|---|---|---|
| 2,371,965 A | 3/1945 | Lehmberg |
| 2,428,451 A | 10/1947 | Emerson |
| 2,444,417 A | 7/1948 | Bierman |
| 2,625,155 A | 1/1953 | Engelder |
| 2,706,983 A | 4/1955 | Matheson et al. |
| 2,882,895 A | 4/1959 | Galeazzi |
| 2,931,356 A | 4/1960 | Schwarz |
| 3,796,216 A | 3/1974 | Schwarz |
| 4,062,357 A | 12/1977 | Laerdal |
| 4,069,516 A | 1/1978 | Watkins, Jr. |
| 4,265,239 A | 5/1981 | Fischer, Jr. et al. |
| 4,328,797 A | 5/1982 | Rollins et al. |
| 4,739,755 A | 4/1988 | White et al. |
| 4,770,169 A | 9/1988 | Schmoegner et al. |
| 4,907,584 A | 3/1990 | McGinnis |
| 4,944,310 A | 7/1990 | Flock et al. |
| 4,928,835 A | 9/1990 | Collette et al. |
| 4,971,051 A | 11/1990 | Toffolon |
| 5,062,421 A | 11/1991 | Burns et al. |
| 5,074,297 A | 12/1991 | Venegas |
| 5,243,971 A | 9/1993 | Sullivan et al. |
| 5,349,949 A | 9/1994 | Shegerin |
| 5,353,789 A | 10/1994 | Schlobohm |
| 5,355,878 A | 10/1994 | Griffiths et al. |
| 5,391,248 A | 2/1995 | Brain |
| 5,429,683 A | 7/1995 | Le Mitouard |
| 5,438,981 A | 8/1995 | Starr et al. |
| 5,540,223 A | 7/1996 | Starr et al. |
| 5,579,761 A | 12/1996 | Yuschak et al. |
| 5,647,357 A | 7/1997 | Barnett et al. |
| 5,649,532 A | 7/1997 | Griffiths |
| 5,662,101 A | 9/1997 | Ogden et al. |
| 5,724,965 A | 3/1998 | Handke et al. |
| 5,918,598 A | 7/1999 | Belfer et al. |
| 5,921,239 A | 7/1999 | McCall et al. |
| 5,935,136 A | 8/1999 | Hulse et al. |
| 5,975,079 A | 11/1999 | Hellings et al. |
| 6,016,804 A | 1/2000 | Gleason et al. |
| 6,112,746 A * | 9/2000 | Kwok ..................... A61B 5/097 128/206.26 |
| 6,192,886 B1 | 2/2001 | Rudolph |
| 6,412,487 B1 | 7/2002 | Gunaratnam et al. |
| 6,412,488 B1 | 7/2002 | Barnett et al. |
| 6,467,483 B1 * | 10/2002 | Kopacko ............... A61M 16/06 128/205.25 |
| 6,467,843 B1 | 10/2002 | Kopacko et al. |
| 6,513,526 B2 | 2/2003 | Kwok et al. |
| 6,626,177 B1 | 9/2003 | Ziaee |
| 6,772,760 B2 | 8/2004 | Frater et al. |
| 6,851,425 B2 | 2/2005 | Jaffree et al. |
| 6,851,428 B2 | 2/2005 | Dennis |
| 7,523,754 B2 | 4/2009 | Lithgow et al. |
| 7,827,990 B1 | 11/2010 | Melidis et al. |
| 7,900,630 B2 | 3/2011 | Geiselhart et al. |
| 7,971,590 B2 | 7/2011 | Frater et al. |
| 8,297,283 B2 | 10/2012 | Hitchcock et al. |
| 8,522,784 B2 | 9/2013 | Ng et al. |
| 8,528,561 B2 | 9/2013 | Ng et al. |
| 8,550,084 B2 | 10/2013 | Ng et al. |
| 8,820,327 B2 | 9/2014 | Melidis et al. |
| 9,375,545 B2 * | 6/2016 | Darkin ................... A61M 16/06 |
| 9,522,246 B2 * | 12/2016 | Frater ..................... A61M 16/06 |
| 2002/0029780 A1 | 3/2002 | Frater et al. |
| 2002/0043265 A1 | 4/2002 | Barnett et al. |
| 2003/0019495 A1 * | 1/2003 | Palkon ................... A61M 16/06 128/206.21 |
| 2003/0089372 A1 | 5/2003 | Frater et al. |
| 2004/0118406 A1 | 6/2004 | Lithgow et al. |
| 2004/0144386 A1 | 7/2004 | Frater et al. |
| 2006/0032504 A1 * | 2/2006 | Burton .................. A61M 16/06 128/207.11 |
| 2006/0042629 A1 | 3/2006 | Geist |
| 2006/0272646 A1 | 12/2006 | Ho et al. |
| 2007/0044804 A1 | 3/2007 | Matula, Jr. et al. |
| 2007/0163600 A1 | 7/2007 | Hoffman |
| 2007/0267017 A1 | 11/2007 | McAuley et al. |
| 2009/0095301 A1 | 4/2009 | Hitchcock et al. |
| 2009/0139526 A1 | 6/2009 | Melidis et al. |
| 2010/0282265 A1 | 11/2010 | Melidis et al. |
| 2013/0037033 A1 | 2/2013 | Hitchcock et al. |
| 2013/0133660 A1 | 5/2013 | Ng et al. |
| 2013/0327333 A1 | 12/2013 | Ng et al. |
| 2014/0338672 A1 | 11/2014 | D'Souza et al. |

FOREIGN PATENT DOCUMENTS

| | | |
|---|---|---|
| EP | 0 334 555 | 9/1989 |
| EP | 0 303 090 | 4/1992 |
| EP | 0 747 078 | 12/1996 |
| EP | 0 853 962 | 7/1998 |
| EP | 1 057 494 | 12/2000 |
| GB | 649689 | 1/1951 |
| JP | 11-000397 | 1/1999 |
| JP | 2003-535657 | 12/2003 |
| NZ | 232296 | 1/1990 |
| NZ | 556043 A | 1/2011 |
| WO | WO 97/00092 | 1/1997 |
| WO | WO 98/04310 | 2/1998 |
| WO | WO 98/34665 | 8/1998 |
| WO | 99/21618 | 5/1999 |
| WO | WO 01/62326 | 8/2001 |
| WO | WO 01/97893 | 12/2001 |
| WO | WO 2004/022146 | 3/2004 |
| WO | WO 2004/071565 | 8/2004 |

(56) References Cited

FOREIGN PATENT DOCUMENTS

| WO | 2005/118042 | 12/2005 |
|---|---|---|
| WO | WO 2005/123166 | 12/2005 |
| WO | WO 2006/074515 | 7/2006 |
| WO | WO 2006/138416 | 12/2006 |
| WO | WO 2007/147088 | 12/2007 |
| WO | WO 2009/108995 | 9/2009 |

OTHER PUBLICATIONS

Notice of Opposition filed Dec. 23, 2016 by Fisher & Paykel Healthcare Limited in New Zealand Application No. 703971 (2 pages).
Deadline for Counterstatement dated Mar. 28, 2017 issued in New Zealand Application No. 703971 (2 pages).
Filing Cover Sheet dated Mar. 27, 2017 from AJ Park in New Zealand Application No. 703971 (1 page).
Amended Notice of Opposition to Grant of Patent dated Mar. 27, 2017 filed by Fisher & Paykel Healthcare Limited in New Zealand Application No. 703971 with Mark-ups (2 pages).
Amended Notice of Opposition to Grant of Patent dated Mar. 27, 2017 filed by Fisher & Paykel Healthcare Limited in New Zealand Application No. 703971 without Mark-ups (2 pages).
Statement of Case dated Mar. 27, 2017 filed by Fisher & Paykel Healthcare Limited in New Zealand Application No. 703971 (14 pages).
Communication regarding Proceeding Halt dated Jul. 3, 2017 issued in New Zealand Application No. 703971, Proceeding No. 3340 (1 page).
Correspondence Requesting Opposition is Put on Hold dated Jun. 22, 2017 filed in New Zealand Application No. 703971, Proceeding No. 3340 by Fisher & Paykel Healthcare Limited (7 pages).
Further Examination Report dated Dec. 11, 2017 issued in New Zealand Application No. 722620 (1 page).
International Search Report for PCT/AU2006/000034, dated Mar. 6, 2006.
U.S. Appl. No. 60/735,823, filed Nov. 14, 2005, first named inventor: Vincent Chu.
International Preliminary Report on Patentability, PCT/AU2006/000034 (dated Jul. 17, 2007).
European Sear Report issued in EP 06 70 4770 (dated Oct. 20, 2009).
Examiner's First Report issued in related Australian Appl. No. 2006206042 (dated Feb. 14, 2011).
Office Action issued in related European Appl. No. 06704770.4 (dated Mar. 28, 2011).
Office Action issued in related Japanese Appl. No. 2007-550638 (dated May 10, 2011).
Office Action issued in related New Zealand Appl. No. 589953 (dated Dec. 22, 2010).
Office Action issued in related Chinese Appl. No. 201010151817.0 (dated Aug. 22, 2011) with English translation.
Examination Report issued in related New Zealand Appl. No. 598811 (dated Mar. 26, 2012).
Notice of Allowance issued in related Japanese Appl. No. 2007-550638 (dated May 8, 2012).
Communication issued in a corresponding European Application No. 06 704 770.4 dated Jun. 18, 2013.
First Examination Report issued in a corresponding New Zealand Application No. 614344 dated Aug. 21, 2013.
Summons to Attend Oral Proceedings issued in a corresponding European Appln. No. 06 704 770.4 dated Jun. 5, 2014.
Decision to Refuse a European Patent Application issued in corresponding Patent Appln. No. 06 704 770.4, dated Oct. 23, 2014.
Amended Notice of Opposition to Grant of Patent filed by Fisher & Paykel Healthcare Limited in New Zealand Patent Application No. 622665 and Statement of Case filed Oct. 30, 2014 (27 pages).
Amended Notice of Opposition to Grant of Patent filed by Fisher & Paykel Healthcare Limited in New Zealand Patent Application No. 622670 and Statement of Case filed Oct. 30, 2014 (27 pages).
Amended Notice of Opposition to Grant of Patent filed by Fisher & Paykel Healthcare Limited in New Zealand Patent Application No. 607032 and Statement of Case filed on Oct. 30, 2014 (27 pages).
Amended Notice of Opposition to Grant of Patent filed by Fisher & Paykel Healthcare Limited in New Zealand Patent Application No. 622666 and Statement of Case filed Oct. 30, 2014 (26 pages).
First Examination Report issued in corresponding New Zealand Application No. 703971 dated Feb. 2, 2015.
First Examination Report dated Feb. 16, 2018 issued in New Zealand Application No. 739403 (3 pages).
Opponent's Bundle of Authorities filed May 28, 2018 by Fisher & Paykel Heathcare Limited in New Zealand Application Nos. 599406 and 703971 (286 pages).
Opponent's Submissions on Adequacy of Counterstatements filed May 28, 2018 by Fisher & Paykel Heathcare Limited in New Zealand Application Nos. 599406 and 703971 (18 pages).
Amended Statement of Case dated Aug. 13, 2018 filed by Fisher & Paykel Healthcare Limited in New Zealand Application No. 703971 (17 pages).
Second Amended Notice of Opposition to Grant of Patent dated Aug. 13, 2018 filed by Fisher & Paykel Healthcare Limited in New Zealand Application No. 703971 (2 pages).

\* cited by examiner

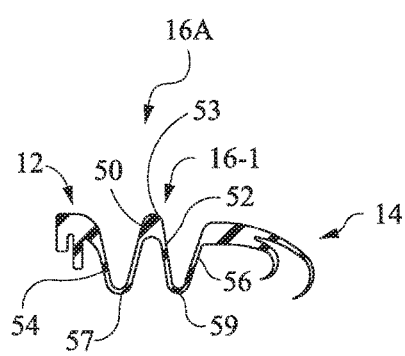
Fig. 4-3
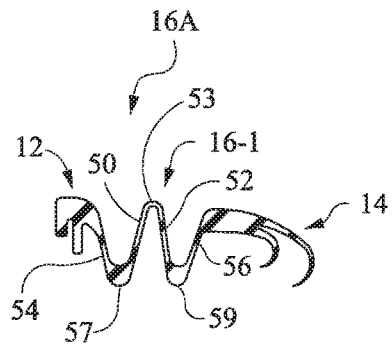
Fig. 4-4
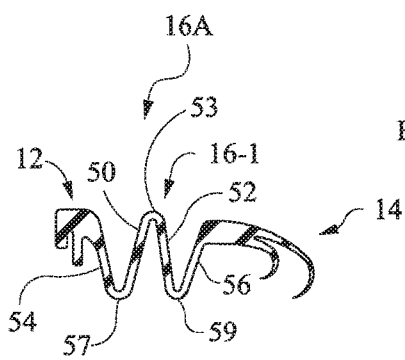
Fig. 4-5
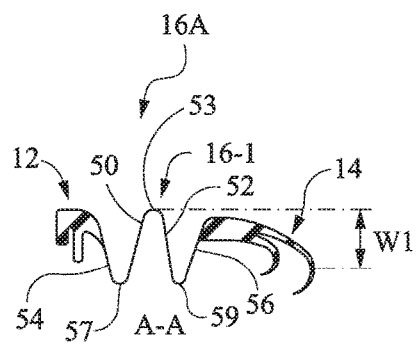
Fig. 4-1
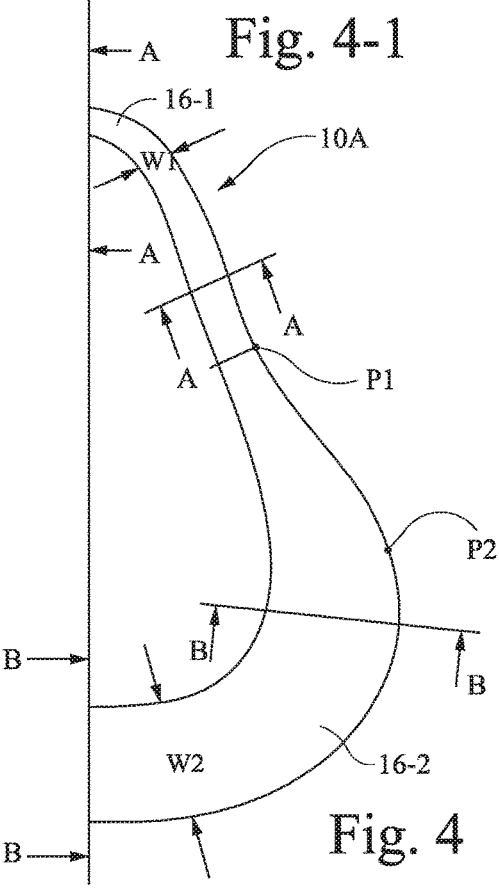
Fig. 4
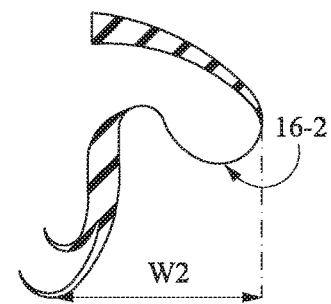
Fig. 4-2   B-B

SECTION G-G

SECTION A-A

SECTION F-F

SECTION E-E

SECTION D-D

SECTION B-B

SECTION C-C

SECTION H-H

RESPIRATORY MASKS WITH GUSSETED CUSHIONS

CROSS-REFERENCE TO RELATED APPLICATIONS

This application is a continuation of U.S. patent application Ser. No. U.S. 13/654,600, filed Oct. 18, 2012, now U.S. Pat. No. 9,308,342, which is continuation of U.S. patent application Ser. No. 11/793,051, filed Dec. 8, 2008, now U.S. Pat. No. 8,297,283, which is the U.S. National Phase of International Application No. PCT/AU2006/000034, filed Jan. 12, 2006, which designated the U.S. and claims the benefit of U.S. Provisional Application No. 60/643,115, filed Jan. 12, 2005, the entirety of each of which is incorporated herein by reference.

Also, PCT Application No. PCT/AU2005/000850, filed Jun. 15, 2005, is expressly incorporated hereinto by reference in its entirety.

FIELD OF THE INVENTION

The present invention relates generally to the field of masks used for respiratory therapy. In especially preferred embodiments, the present invention relates to respiratory masks having a gusseted cushion.

BACKGROUND OF THE INVENTION

Facial masks are well known for use in continuous positive airway pressure (CPAP) treatment of various respiratory ailments and sleep disordered breathing (SDB), such as, for example, obstructive sleep apnea (OSA) and/or other ventilatory assistance treatments such as noninvasive positive pressure ventilation (NPPV). See, for example, U.S. Pat. No. 4,944,210, the entire content of which is expressly incorporated hereinto by reference. While the present invention will be described below with reference to a full facial mask for use in CPAP treatment, it will be understood that such a reference is non-limiting and is directed toward a particularly preferred embodiment of the present invention. Thus, the various characteristics and advantages of the present invention could equivalently be embodied in another type of mask, such as a nasal mask, or another type of NPPV therapy.

Apparatus for the treatment of SDB generally involves a blower which delivers a supply of air at positive pressure to a patient interface via a conduit. The patient interface may take several forms, such as a nasal mask assembly and a nasal and mouth mask assembly (i.e., a full face mask). Patients typically wear a mask assembly while sleeping to receive the NPPV therapy.

Mask assemblies typically include a rigid shell or frame and a soft face-contacting cushion. The cushion cushions the rigid frame from the patient's face, and provides a seal with the patient's face. The frame and cushion define a cavity which receives the nose or nose and mouth. The frame and cushion are held in position on the patient's face by a headgear assembly. The headgear assembly typically comprises an arrangement of straps which pass along both sides of the patient's face to the back or crown of the patient's head.

One problem that arises with existing masks used for CPAP treatments is that over-tightening of the mask straps results in compression of the mask against the wearer's face which may therefore apply undue pressure force against certain of the wearer's facial features, such as the wearer's nose. A poorly fitting mask can leak when pressurized which encourages a patient to tighten the headgear straps excessively which, in turn leads to discomfort, marks on the face and in some cases facial sores.

The cushion of a patient mask interface can play a key role in the comfort and effectiveness of therapy. The nasal bridge area of the patient's face has been identified as being particularly sensitive and thus a mask design needs to pay particular attention to such region.

The issue of mask comfort and effectiveness is particularly apparent when treatment pressure varies, for example, when a patient uses an automatic positive airway pressure (APAP) device such as those commercially available from ResMed Limited under the tradename AUTOSET. When the pressure varies, patients may set the headgear tension for the highest pressure, which thereby leads to unnecessarily high tension being experienced at lower pressures.

To address such problems, mask systems that vary the sealing force with treatment pressure have been developed, including a nasal mask cushion having a gusset portion, as evidenced by U.S. Published Patent Application 2002/0029780; U.S. Pat. No. 6,772,760 and U.S. Published Patent Application US 2004/0118406, the entire content of each being expressly incorporated hereinto by reference. A commercial embodiment of the inventions described in such patent publications is the ACTIVA™ mask system available from ResMed Limited.

U.S. Pat. No. 5,074,297 (the entire content of which is expressly incorporated hereinto by reference) describes a respiratory mask assembly for use with intermittent positive pressure breathing treatment and is said to facilitate the formation and automatic adjustment of the seal between a patient's face and a facial unit of the respiratory mask.

While the prior proposals for adjustable mask cushions may be satisfactory for their intended purposes, improvements are still needed, especially for a full face mask patient interface.

SUMMARY OF THE INVENTION

Broadly, one embodiment of the present invention is directed to full face masks for use in respiratory therapy wherein a gusset portion is interposed between the mask cushion and the mask frame. The gusset portion thereby allows for relative movement of the mask frame to occur towards and away from a patient's face to ensure the integrity of sealing contact between the cushion and the patient's facial features and to maintain a desired comfort level.

The gusset portion in accordance with the present invention provides several benefits. For example, the gusset portion utilizes the pressure in the mask acting on its increased surface area to provide a force to maintain the face-contacting portion of the cushion in sealing contact with the patient's face. Of course, the gusset may include a predetermined spring constant that can also affect the force applied to seal against the user's skin. Additionally, the gusset portion provides in effect a decoupling joint between the face-contacting portion of the cushion and the mask shell thereby allowing some relative movement to occur between the mask and the cushion contacting the patient's face. This arrangement substantially protects the seal from undue disturbance when the mask or mask shell is tilted; the facial muscles are relaxed, patient movement occurs, and/or movement of the gas supply tube occurs. This decoupling joint provided by the gusset also allows additional travel between the mask shell and the lower cushion which reduces the precision by which the strap length must be maintained.

The gusset portion of the present invention is especially beneficial in the context of a full face mask since it has at least one perimetrical section which includes generally laterally projecting exterior and interior gusset sections. Both laterally extending exterior and interior gusset sections provide flexibility and increase the allowable travel of the mask frame from the cushion. The laterally projecting exterior section also provides additional sealing pressure to the cushion depending on treatment pressure. Most preferably, the incorporation of the laterally exterior projecting gusset section increases the projected surface area on the patient's face by at least about 260% compared to the projected surface area of the face-contacting portion of the cushion alone. For example, in an embodiment, the projected surface area of the face-contacting portion alone is about 50 cm$^2$ and the projected surface area of the gusset section alone is in the range of 30-90 cm$^2$, preferably about 80 cm$^2$. Thus, the gusset section adds about 80 cm$^2$ extra area to the cushion or about 160% (80/50) extra area compared to the cushion alone. As a result, the total projected surface area of the gusseted cushion is equal to the summation of the face-contacting portion and the gusset section which is in the range of 80-140 cm$^2$, preferably about 130 cm$^2$ (80+50), and this total area is about 260% (130/50) of the projected surface area of the face-contacting portion alone.

One aspect of the gusseted cushion according to the present invention is the greater projected area that may be achieved in a particular facial region of the patient which leads to additional sealing force per unit mask pressure that may be obtained at such region. By varying the widthwise extent that the gusset projects laterally outwardly around the perimeter of the mask, the amount of pressure-dependent additional sealing force can be varied since pressure acts upon the additional area from the sealing point of the cushion on the face to the exterior of the gusset and provides a force on the cushion. For example, according to an aspect of the present invention, the sealing force may be reduced in sensitive facial areas of the patient, such as the region of the patient's nasal bridge by reducing the widthwise extent of the gusset in this region.

The amount of additional area that the laterally outwardly extending gusset is required to project is also dependent upon the treatment pressure. A relatively large area $A_g$ (e.g. 300 cm$^2$ when compared to the projected area of the cushion $A_c$ of 50 cm$^2$, see FIG. 8) might form a suitable seal at a low pressure of about 4 cmH$_2$O, but may be excessive at about 20 cmH$_2$O. The overall sealing pressure on the cushion is a combination of the strap tightness and the additional area projected outside the sealing point of the cushion. It has been found that an overall sealing pressure of about 3 kg total force on the entire cushion seal applies excessive force to the patient and hence a projected gusset area should be such that the overall sealing pressure is less than 3 kg. More specifically, the width of the gusset should have a preferred projected area $A_g$ onto the patient's face of approximately 130 cm$^2$ when the invention is embodied in a full face mask.

Another aspect of the gusset is the travel available in a particular patient facial region. Travel allows movement to occur between the frame contacting portion and the patient contacting portion of the cushion between which the gusset is disposed. In general, a cushion in accordance with the invention allows substantially the same amount of travel around the entirety of the cushion's perimeter so that the frame and patient contacting portions can remain generally parallel. This is achieved by varying the width of the interior projecting gusset or gussets to maintain the amount of travel regardless of the width of the exterior projecting gusset which is tailored to meet the particular sealing force requirements of the facial region. In use there may in fact be non-parallel travel movement of the frame relative to the patient's face due to the inherent flexibility of their material of construction. In this regard, the gusseted cushions of the present invention most preferably provide between about 5 mm to about 25 mm, advantageously about 16 mm (+/−1 mm), of travel distance when embodied in a full face mask.

The present invention may be embodied in a cushion for a respiratory mask assembly having a frame-connecting portion, a face-contacting portion, and a gusset portion disposed between and joining the frame-connecting and face-contacting portions. The gusset portion preferably includes at least one perimetrical region which has a laterally projecting exterior gusset section and a laterally projecting interior gusset section.

According to one aspect, the laterally projecting exterior and interior gusset sections are disposed about the entire perimeter to the gusset portion so as to establish a substantially constant widthwise dimension thereof about the gusset's entire perimeter. According to another aspect, the laterally projecting exterior and interior gusset sections of the gusset project only along a lower perimetrical region thereof so that the gusset portion has a widthwise dimension which varies about its perimeter.

In another aspect, the gusset portion has a minimum widthwise dimension at an upper perimetrical region thereof, a maximum widthwise dimension at a lower perimetrical region thereof, and widthwise transitions joining said upper and lower perimetrical regions thereof. The widthwise transitions may be either curvilinear or linear.

Another aspect of the present invention is a cushion for a respiratory mask having a frame-connecting portion, a face-contacting portion, and a gusset portion disposed between and joining the frame-connecting and face-contacting portions, wherein said gusset portion has a perimeter with a widthwise dimension which varies between at least one region and another perimetrical region thereof. In a preferred aspect, the gusset portion has a minimum widthwise dimension at an upper perimetrical region thereof, a maximum widthwise dimension at a lower perimetrical region thereof, and widthwise transitions (which may be curvilinear or linear) joining such upper and lower perimetrical regions thereof.

In one specific aspect, the cushion of the present invention substantially zero widthwise dimension at said upper perimetrical region thereof. In accordance with another aspect of the invention, each of the minimum and maximum widthwise dimensions is substantially constant along the upper and lower perimetrical regions, respectively.

According to another aspect, the invention has an upper perimeter region which occupies between about 15% to about 30% of the entire perimeter of the cushion, a lower perimeter region which occupies between about 50% to about 70% of the entire perimeter of the cushion, and transition regions which occupy between about 10% to about 30% of the entire perimeter of the cushion.

These and other aspects and advantages will become more apparent after careful consideration is given to the following detailed description of the preferred exemplary embodiments thereof.

BRIEF DESCRIPTION OF THE DRAWINGS

Reference will hereinafter be made to the accompanying drawings, wherein like reference numerals throughout the various FIGURES denote like structural elements, and wherein:

FIGS. 1-1 to 1-4 show various views of a full facial mask assembly providing patient interface for respiratory therapy having an embodiment of a gusseted cushion according to the present invention, wherein FIG. 1-1 is a front plan view thereof, FIG. 1-2 is a front perspective view thereof, FIG. 1-3 is left side elevational view thereof, and FIG. 1-4 is a rear perspective view thereof;

FIG. 2 is a schematic partial rear plan rear view (patient side) of a gusseted cushion employed in the face mask assembly depicted in FIGS. 1-1 to 1-4;

FIG. 2-1 is a cross-section of the cushion depicted in FIG. 2 as taken along line A-A therein;

FIGS. 2-2 to 2-4 are alternative cross-sections of the cushion depicted in FIG. 2 as taken along line A-A therein;

FIGS. 3-1 to 3-3 show various views of a full face mask assembly providing patient interface for respiratory therapy having another embodiment of a gusseted cushion according to the present invention, wherein FIG. 3-1 is a front plan view thereof, FIG. 3-2 is a front perspective view thereof, FIG. 3-3 is right side elevational view thereof;

FIG. 4 is a schematic partial rear plan rear view (patient side) of a gusseted cushion employed in the mask assembly depicted in FIGS. 3-1 to 3-3;

FIGS. 4-1 and 4-2 are cross-sections of the cushion depicted in FIG. 4 as taken along lines A-A and B-B therein, respectively;

FIGS. 4-3 to 4-5 are alternative cross-sections of the cushion depicted in FIG. 4 as take along line A-A therein;

FIGS. 5-1 to 5-3 are various views of a gusseted cushion according to another embodiment of the present invention, wherein FIG. 5-1 is a top elevation view thereof, FIG. 5-2 is a right side elevation view thereof, and FIG. 5-3 is a bottom elevation view thereof;

FIGS. 6-1 to 6-8 are various cross-sections of the cushion depicted in FIG. 6 wherein, FIG. 6-1 is a cross-section taken along line G-G therein; FIG. 6-2 is a cross-section taken along line A-A therein; FIG. 6-3 is a cross-section taken along line F-F therein; FIG. 6-4 is a cross-section taken along line E-E therein; FIG. 6-5 is a cross-section taken along line D-D therein; FIG. 6-6 is a cross-section taken along line B-B therein; FIG. 6-7 is a cross-section taken along line C-C therein; and FIG. 6-8 is a cross-section taken along line H-H therein;

FIG. 7 is a plot of sealing force (Kg) on a patient's face from the cushion versus displacement distance of the mask frame towards the patient's face (i.e., from a fully expanded state of the gusset to a fully compressed state of the gusset);

FIG. 8 is a schematic view illustrating the relation between the projected area of the gusset $A_g$ and the projected area of the face-contacting portion of the cushion $A_c$.

DETAILED DESCRIPTION OF PREFERRED EMBODIMENTS

First Cushion Embodiment

Figure 1:
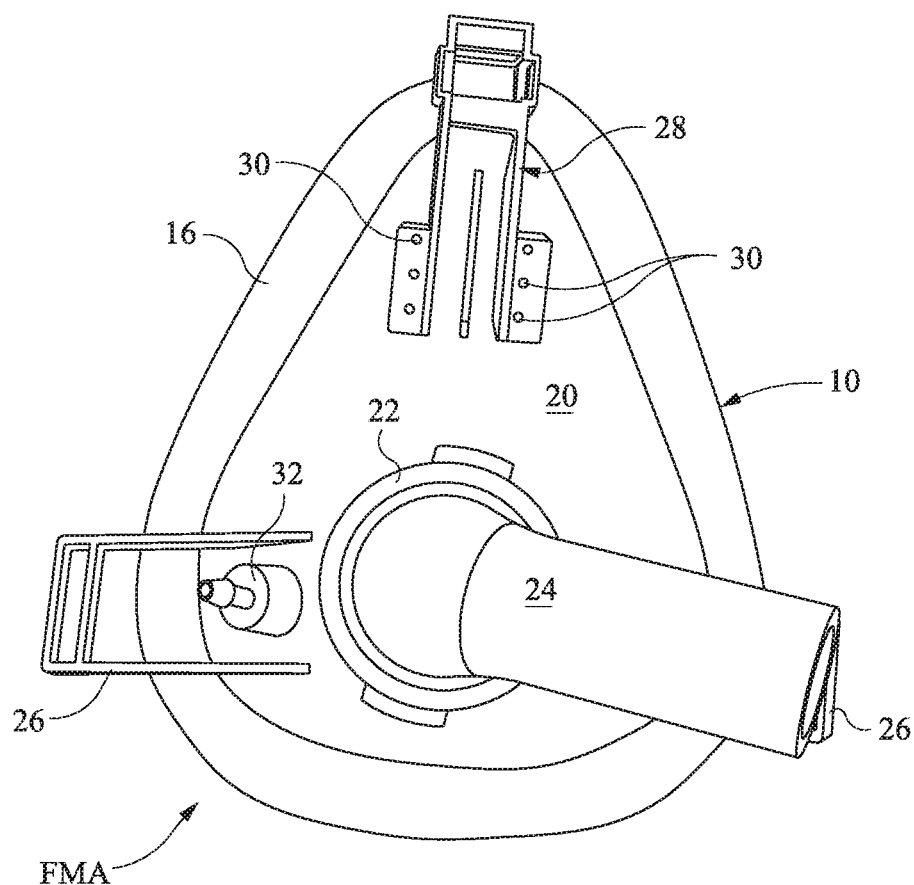

An exemplary embodiment of a full facial mask assembly FMA which includes a gusseted cushion 10 according to one embodiment of the present invention is depicted in accompanying FIGS. 1-1 to 1-4. The mask assembly FMA includes a mask frame 20 provided with a connection port 22 to which an elbow connector 24 associated with a gas supply conduit may be coupled to allow breathable gas under pressure to be supplied to the mask assembly FMA. The cushion 10 includes distal mask-connecting portion 12.1 which connects the cushion 10 to the mask frame 20, a proximal face-contacting portion 14 and an intermediate gusset portion 16 is between or joining the distal and proximal portions 12.1, 14, respectively. The mask cushion 10 may also include a reinforcing member 12 that supports one or more sidewalls of the cushion towards the face-contacting portion 14.

Strap connectors 26 extend laterally from the mask frame 20 so as to allow attachment of straps associated with a conventional headgear assembly (not shown) and thereby permit the mask assembly FMA to be secured to a wearer's head when in use. The mask frame 20 may also be provided with a receiver 28 which is adapted to receive a slide bar associated with a forehead support assembly (not shown), for example, a forehead support assembly of the variety disclosed in commonly owned U.S. Provisional Patent Application Ser. No. 60/735,823, filed Nov. 14, 2005, the entire content of which is expressly incorporated hereinto by reference. A number of vents 30 may be provided so as to allow gas exhaled by the patient to vent to atmosphere. In addition, an auxiliary port 32 may be provided so as to allow the introduction of an auxiliary breathable gas to the mask interior as may be desired, or the port 32 may allow for the measure of pressure within the interior of the mask.

Figures 1, 2:
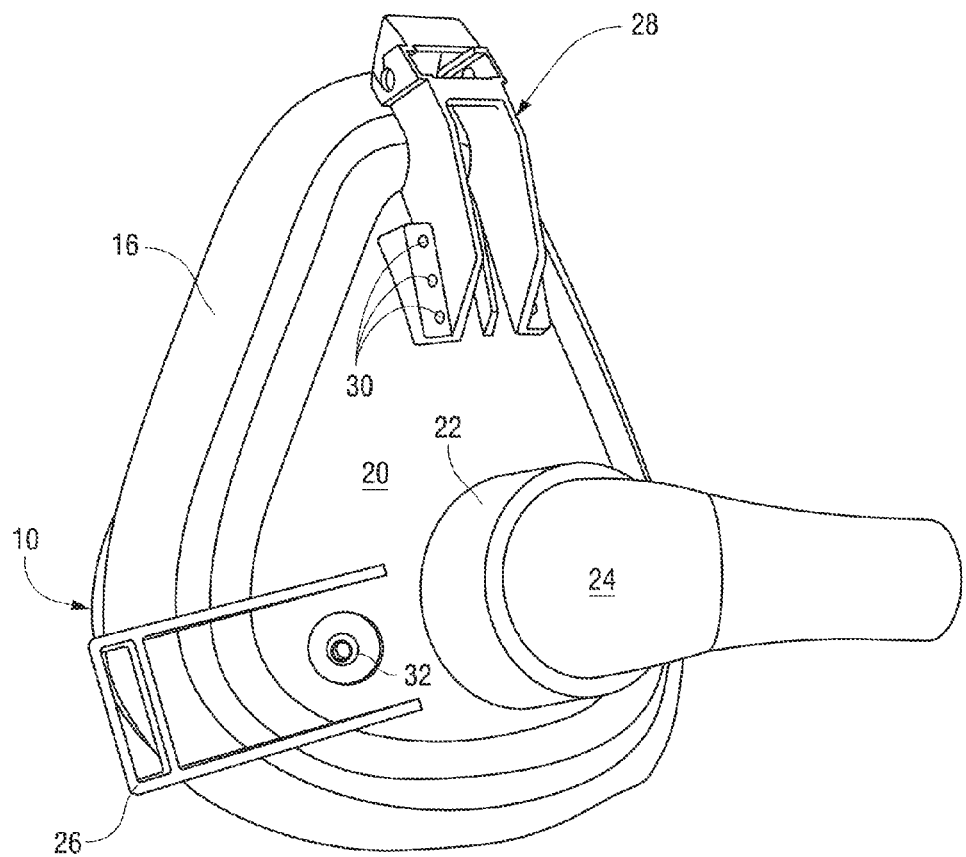

Accompanying FIG. 2 and the cross-section thereof as depicted in FIG. 2-1 show one embodiment of the gusset portion 16 in accordance with the present invention. (Note that FIG. 2-1 does not include reinforcement member 12.) In this regard, the footprint area of the full face mask is generally triangular with the apex thereof at the bridge region of the patient's nose and a base region located generally between the patient's mouth and chin regions. The cushion 10 is similarly triangularly shaped. As shown in FIG. 2, the gusset portion 16 has a substantially constant cross-sectional configuration as depicted in FIG. 2-1 about its entire perimeter. Stated another way, the gusset portion 16 has a substantially constant lateral dimension about the entirety of its generally triangular perimeter which thereby projects a substantially constant cross-sectional area onto the patient's face.

In the embodiment depicted in FIG. 2 and the cross-section thereof depicted in FIG. 2-1, the gusset portion 16 is in the form of an accordion fold having a laterally projecting exterior gusset section 40 and a laterally projecting interior gusset section 42. The laterally projecting exterior and interior gusset sections 40, 42 thus establish respective widthwise dimensions $W_e$, $W_i$ which in use establish the amount of travel and flexibility the gusset provides. The dimension W relating to the exterior gusset section (measured from the cushion contact point to the exterior of the gusset) establishes an area projected on the patient's face $A_g$ which is about 130 cm$^2$ or about 260% greater than the projected surface area (about 50 cm$^2$) of the face-contacting portion of the cushion $A_c$ alone as shown in FIG. 8. For example, in an embodiment, the projected surface area of the face-contacting portion $A_c$ alone is about 50 cm$^2$ and the projected surface area of the gusset section ($A_g$-$A_c$) alone is in the range of 30-90 cm$^2$, preferably about 80 cm$^2$ as shown in FIG. 8. Thus, the gusset section adds about 80 cm$^2$ extra area to the cushion or about 160% (80/50) extra area. As a result, the total projected surface area of the gusseted cushion $A_g$ is equal to the summation of the face contacting portion and the gusset section which is in the range of 80-140 cm², preferably about 130 cm² (80+50), and this total area is about 260% (130/50) of the projected surface area of the face-contacting portion of the cushion $A_c$ alone. These dimensions are exemplary in nature to demonstrate the relevant projected areas.

It is to be understood that the projected surface areas and associated percentage calculations described herein are merely exemplary and other sizes and percentages are possible depending on application. For example, the sizes and percentages described above may be for a medium sized gusseted cushion, and the sizes and associated percentage calculations may be applied proportionally to other sized cushions, e.g., extra small, small, and large.

It will be observed that the gusset portion 16 according to the embodiment depicted in FIG. 2 includes, in order from the mask connecting portion 12 toward the face-contacting portion 14, the exterior gusset section 40 extending generally laterally outwardly and terminating at an exterior tip section 44, a connecting gusset section 46 extending from the tip section 44 generally inwardly and terminating at an interior tip section 48, and the interior gusset section 42 extending generally laterally from interior tip section 48 to the base 14.1 of face-contacting portion 14.

Figures 1, 2, 3:
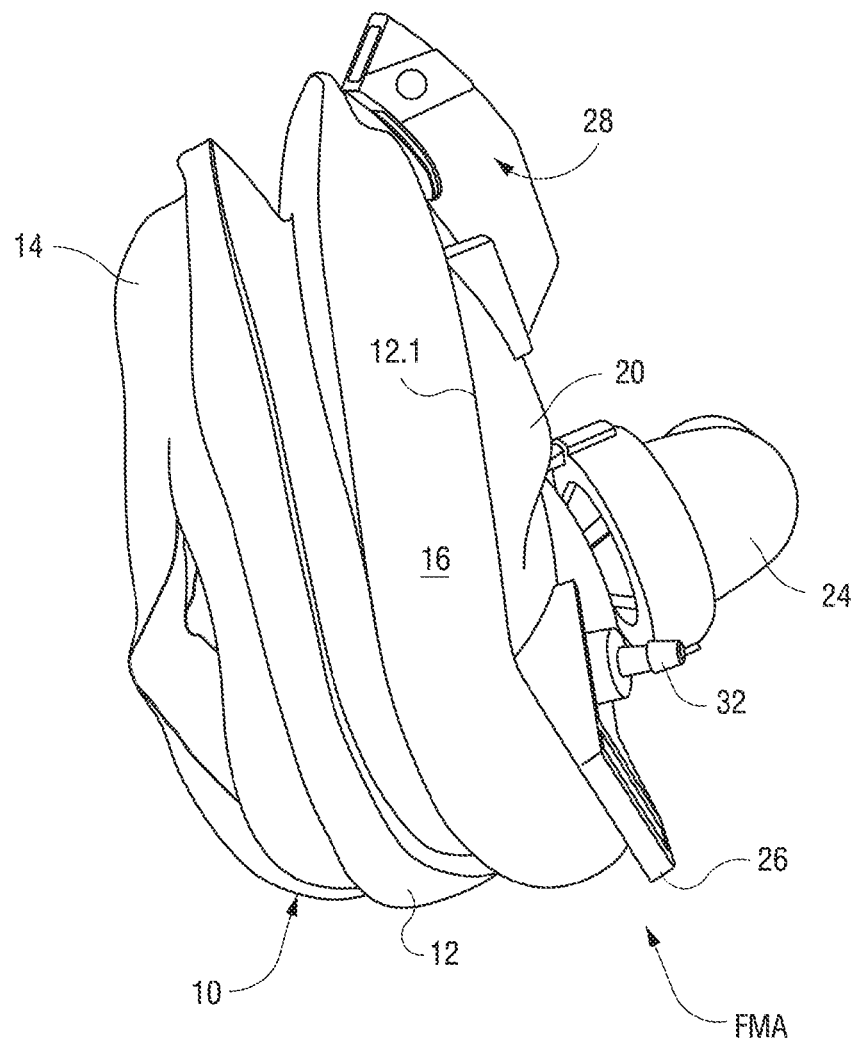
Figures 1, 2, 3, 4:
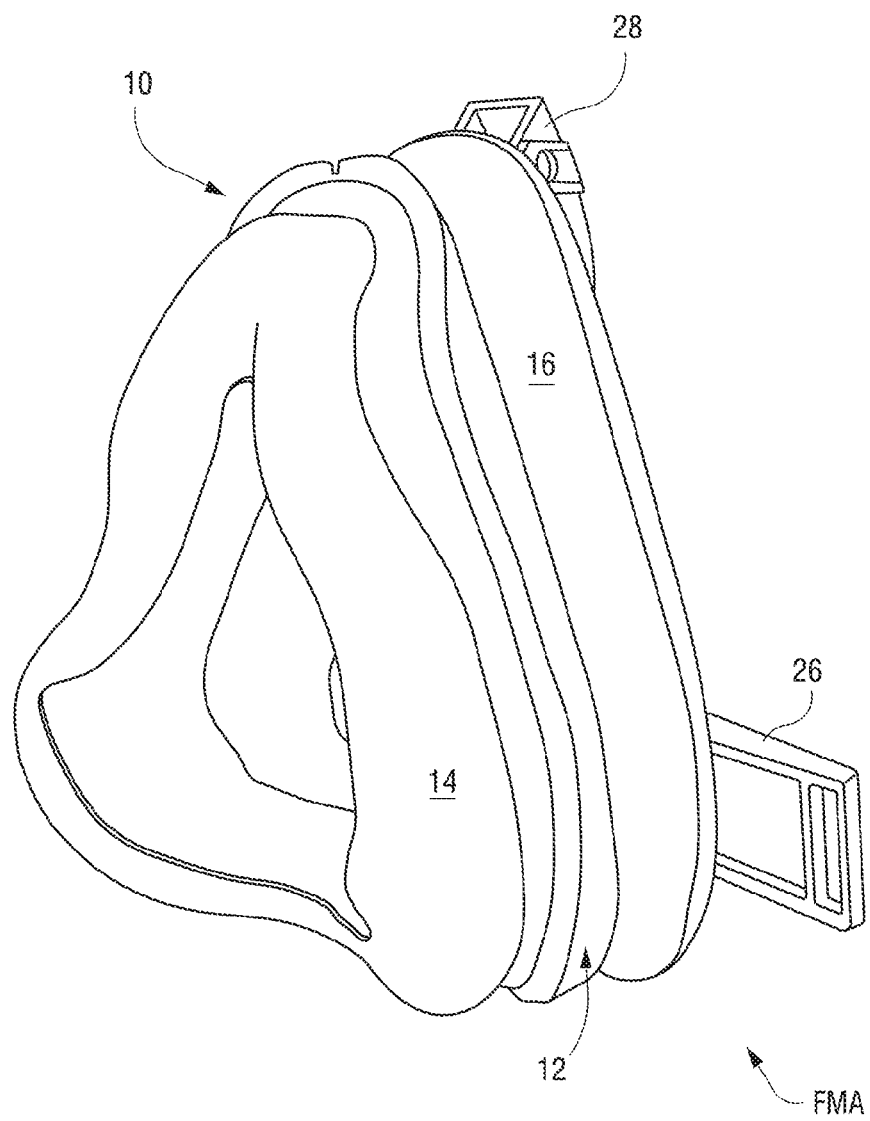
Figures 1, 2:
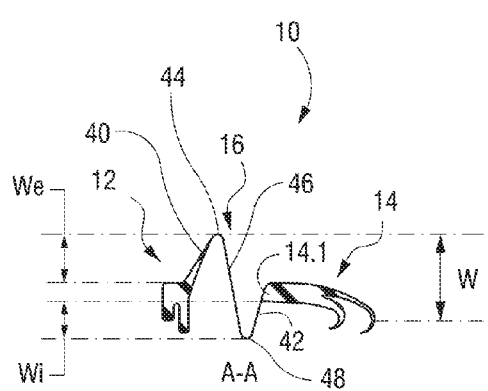
Figure 2:
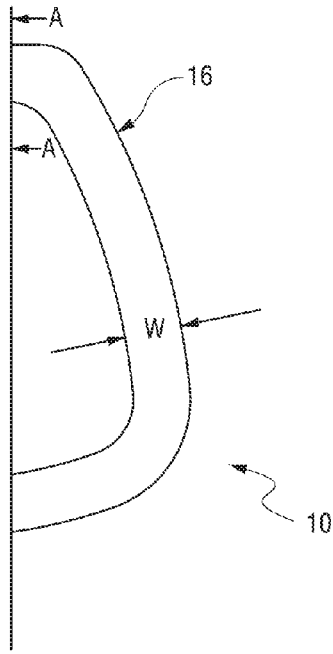
Figure 2:
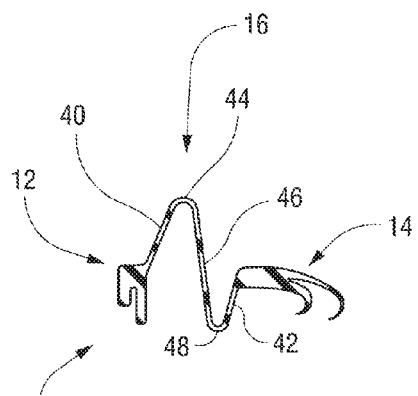
Figures 2, 3:
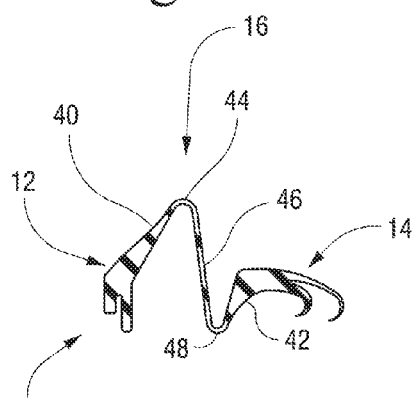
Figures 2, 3, 4:
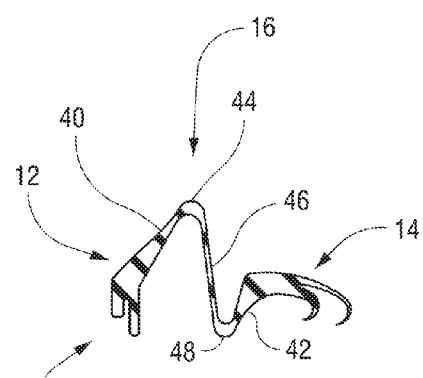
Figures 1, 3:
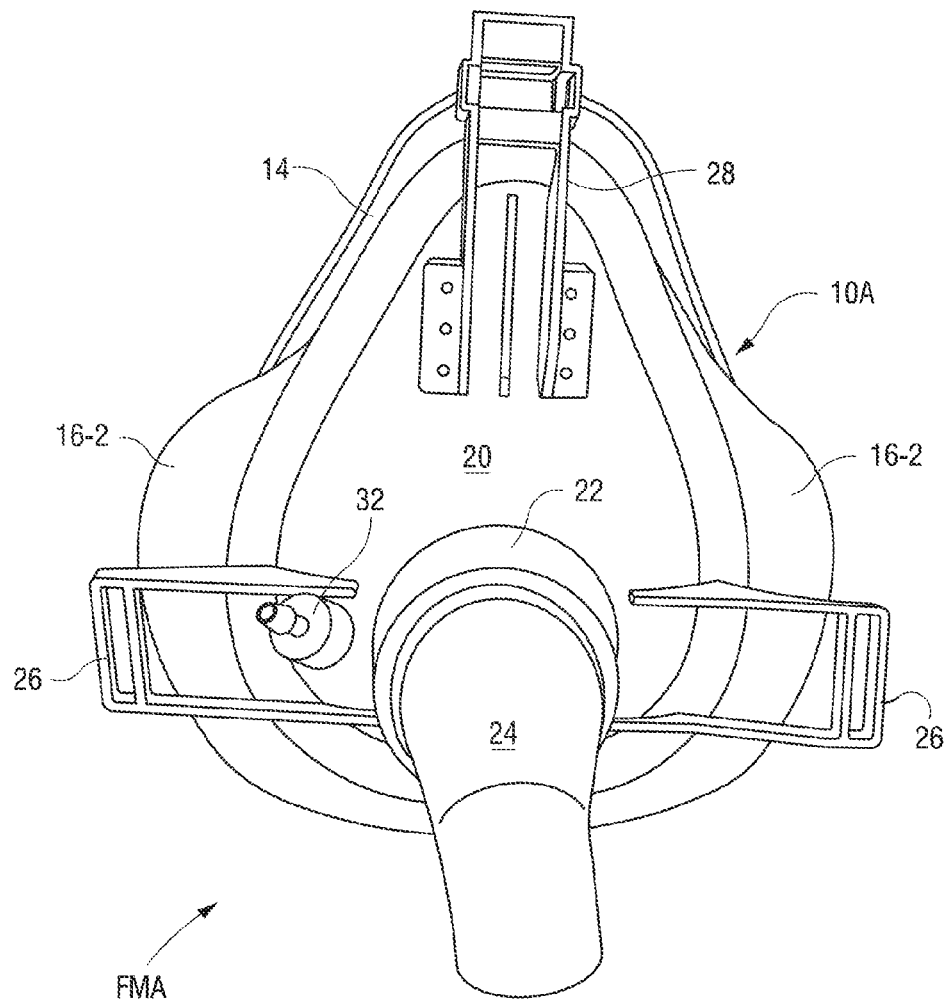
Figures 2, 3:
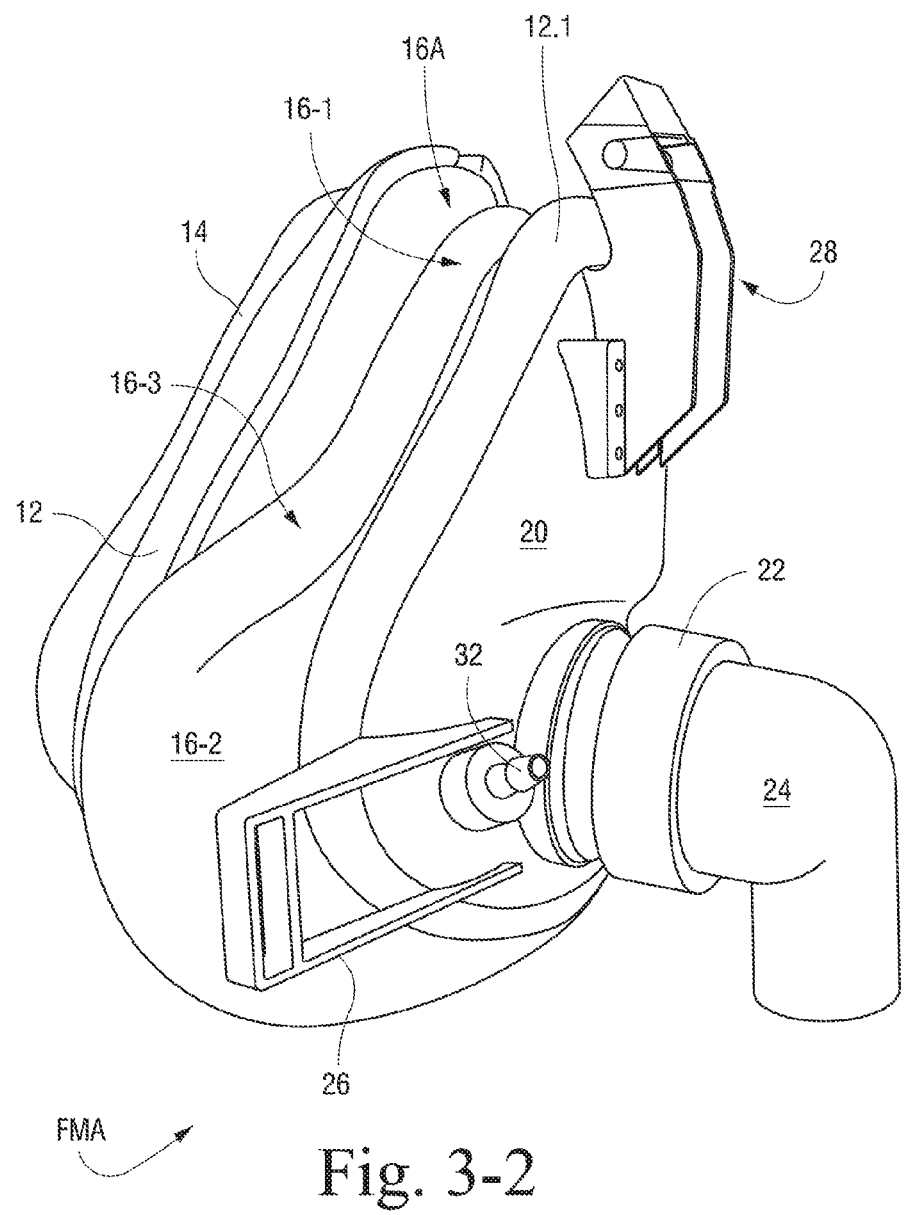
Figure 3:
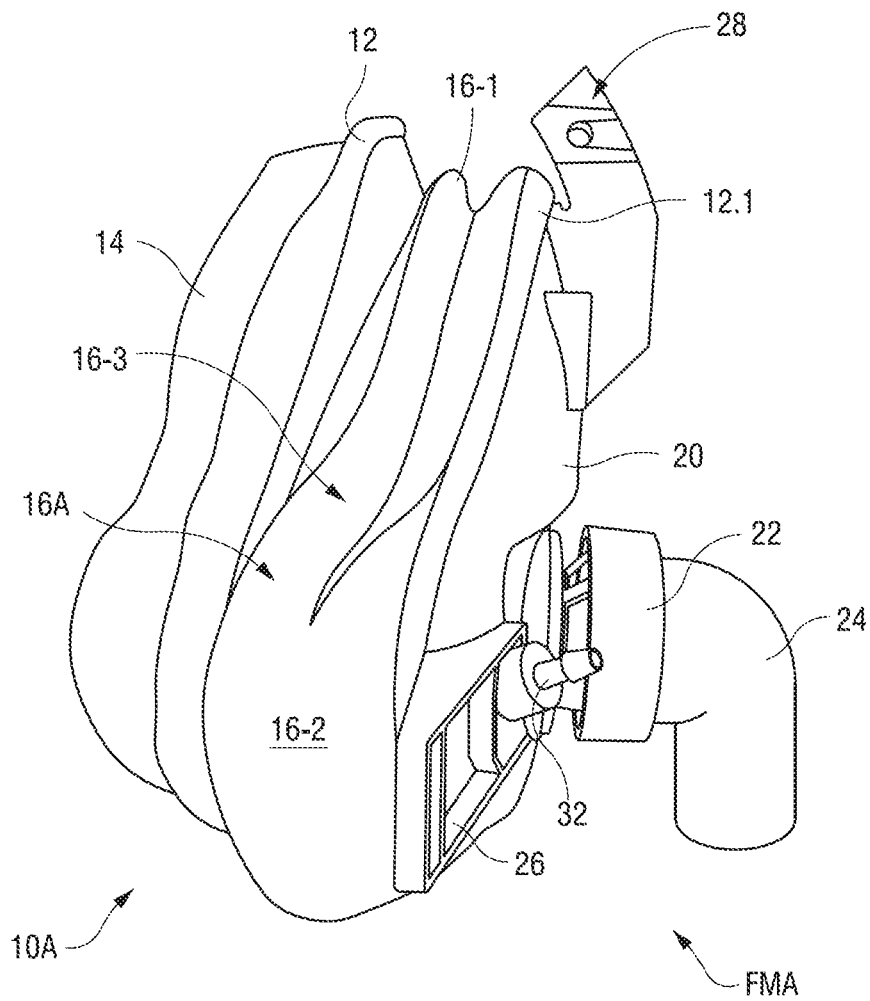

Accompanying FIGS. 2-2 to 2-4 depict alternative cross-sections that may be provided with the gusset portion 16. In this regard, any one cross-section or combination of cross-sections depicted in FIGS. 2-2 to 2-4 may be employed.

It will be observed in FIG. 2-2 that the thickness of each gusset section 40, 42 and 46 is substantially thicker as compared to the embodiment shown in FIG. 2-1. Preferably, the sections 40, 42 and 46 of the gusset portion 16 shown in FIG. 2-2 have a substantially uniform thickness of between about 0.5 mm to about 1.0 mm, whereas the thickness of such comparable sections shown in FIG. 2-1 is about 0.5 mm or less.

Alternatively or additionally, the extremities of the sections 40 and 42 where each joins the mask-connecting portion 12 and the face-contacting portion 14, respectively, may be thickened as shown in FIG. 2-3. Again, alternatively or additionally, the inverted portion of the tip section 44 and the everted portion of the tip section 48 may include a thickened region as shown in FIG. 2-4. The relative thickness of the tip sections 44 and/or 48 may thus be varied as compared to the sections 40, 42 and 46 by the mask designer to achieve desired functions, such as the resiliency or amount of spring force inherently possessed by the gusset portion 16.

Second Cushion Embodiment

A full facial mask assembly FMA employing another embodiment of a gusseted cushion 10A in accordance with the present invention is depicted in FIGS. 3-1 to 3-3 and FIGS. 4, 4-1 and 4-2. In this regard, structural components that are similar to those discussed previously have been shown with the same reference numerals. Thus, a detailed discussion of such similar structural components will not be repeated.

As can be seen in FIG. 4, the gusseted cushion 10A has gusset section 16A provided with a relatively narrow or constant width region 16-1 from a location P1 adjacent a patient's nose and around the patient's nasal bridge region. The gusset section 16A also has a maximal width region 16-2 from a location P2 generally adjacent a patient's mouth region around the base of the cushion 10A. In this regard, compare the width dimensions W1 and W2 (i.e., defining respective projected areas) shown in FIG. 4 for each of the regions 16-1 and 16-2, respectively. The width dimensions W1 and W2 are measured from the cushion contact point to the exterior of the gusset. A transition region 16-3 curvilinearly joins the regions 16-1 and 16-2 between points P1 and P2.

The non-uniform width regions W1 and W2 thus have the benefits of providing less visual obstruction near the eye region of the patient and less force applied at the patient's nasal bridge region due to the presence of the minimal width region W1 thereat. In addition, the center of the applied force against the patient's face is positioned lower as compared to the substantially constant width gusseted cushion 10 as discussed previously due to the greater projected width area being located physically lower in the gusseted cushion 10A.

Thus, as depicted in FIG. 4-1 there is little or no projected area in the gusset in the nasal bridge region, although travel of the cushion/frame is still permitted due to its generally W-shaped or concertina-type fold establishing a pair of exterior gusset sections 50, 52 connected to one another at a tip section 53, and a pair of interior gusset sections 54, 56 connected to the gusset sections 50, 52 at tips 57 and 59, respectively. However, in contrast, the gusset cross-section depicted in FIG. 4-2 has substantially greater width W2 due to the generally sinusoidal shape of the gusset section 16-2 thereof, and hence a substantially greater projected area onto a patient's face as compared to the width W1 of gusset section 16-1 near the patient's nasal region.

Figures 1, 5:
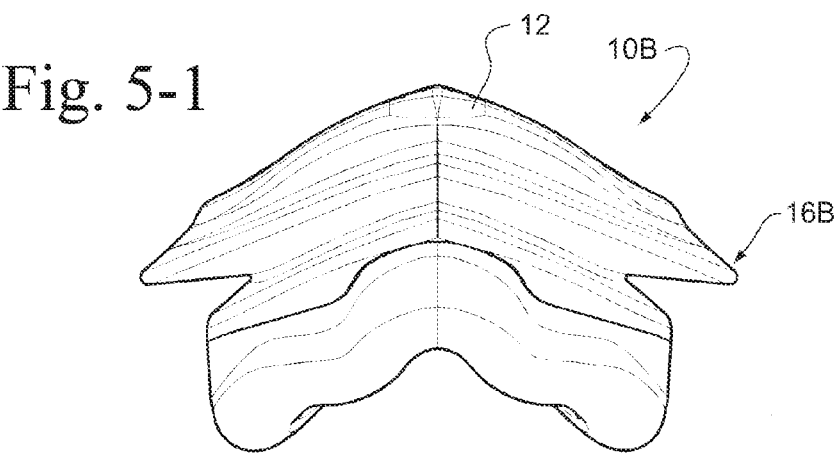
Figures 2, 5:
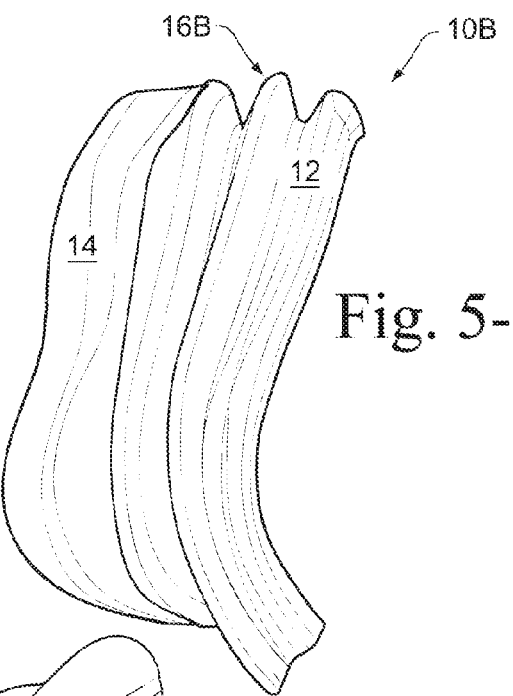
Figures 3, 5:
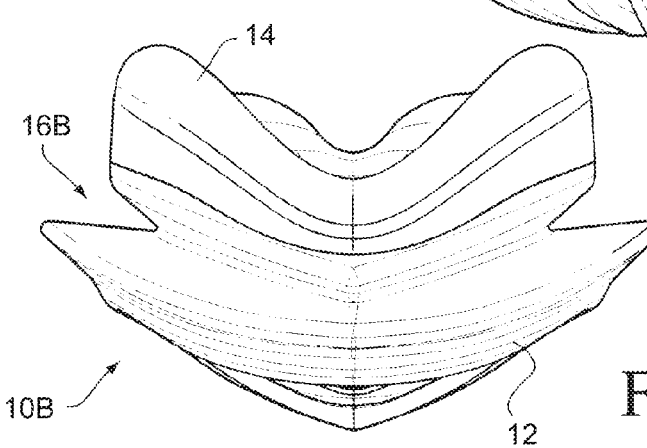

Accompanying FIGS. 4-3 to 4-5 depict alternative cross-sections that may be provided with the gusset portion 16A. In this regard, cross-sections depicted in FIGS. 4-3 to 4-5 may advantageously be employed in gusset sections 16-1 and/or 16-3 so as to provide for the desired degree of relative resiliency thereof. Moreover, any one cross-section or combination of cross-sections as depicted in FIGS. 4-3 to 4-5 may be employed as desired.

In FIG. 4-3 it will be observed that the thickness of the tip section 53 is greater as compared to the other tip sections 57 and 59. Alternatively or additionally, the extremities of the apex of tip sections 57 and 59 may each be thickened relative to the other gusset sections as shown in FIG. 4-4. Again, alternatively or additionally, each gusset section 50-59 according to the alternative cross-section depicted in FIG. 4-5 is substantially thicker as compared to the embodiment shown in FIG. 4-1. In this regard, the thickness of sections 50-59 depicted in FIG. 4-5 is preferably between about 0.5 mm to about 1.0 mm, whereas the thickness of such comparable sections shown in FIG. 4-1 is about 0.5 mm or less.

Third Cushion Embodiment

Another embodiment of a gusset cushion 10B in accordance with the present invention is depicted in FIGS. 5-1 to 5-3, FIG. 6 and the cross-sections thereof shown in FIGS. 6-1 to 6-8. In this regard, as is perhaps most clearly shown in FIG. 6, the gusset cushion 10B is comprised of upper and lower arcuately shaped gusset regions 16B-1 and 16B-2 which are joined to one another by a substantially linear transition region 16B-3.

Figure 6:
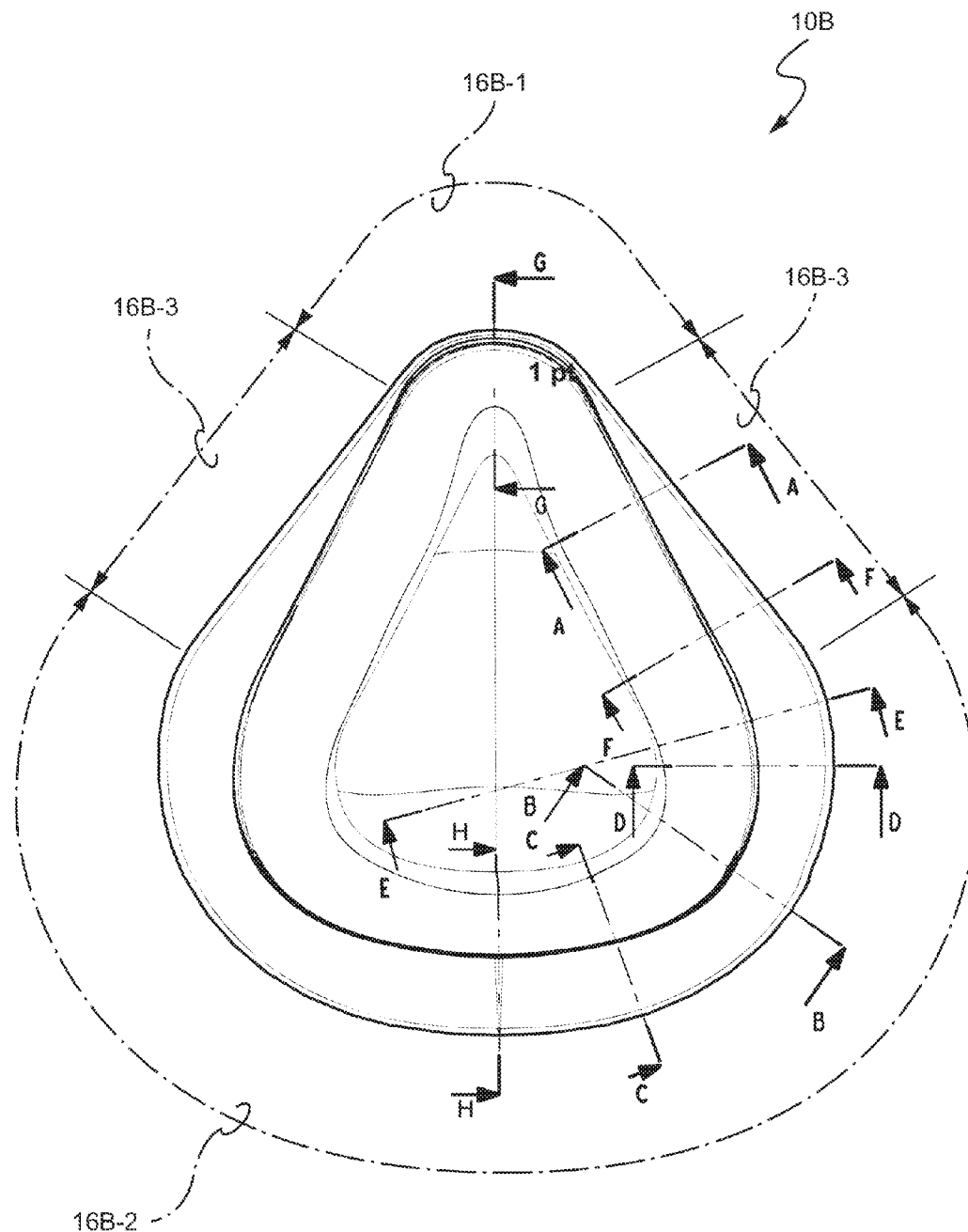
FIG. 6 is a schematic partial rear plan rear view (patient side) of the gusseted cushion depicted in FIGS. 5-1 to 5-3.
Figures 1, 6:
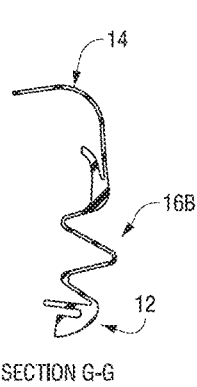
Figures 2, 6:
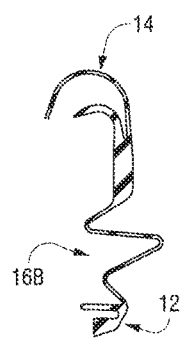
Figures 3, 6:
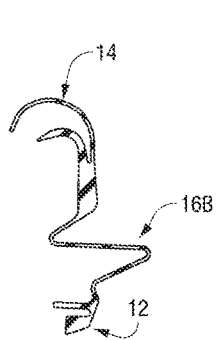
Figures 4, 6:
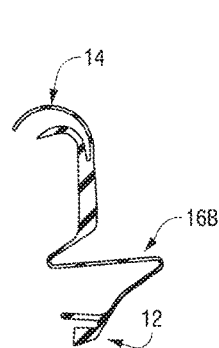
Figures 5, 6:
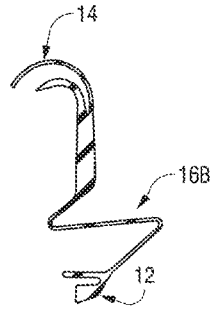
Figure 6:
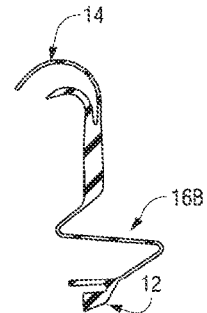
Figures 6, 7:
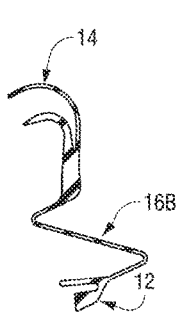
Figures 6, 7, 8:
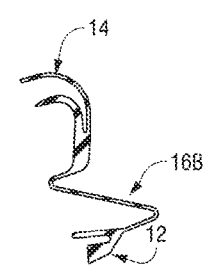
Figure 7:
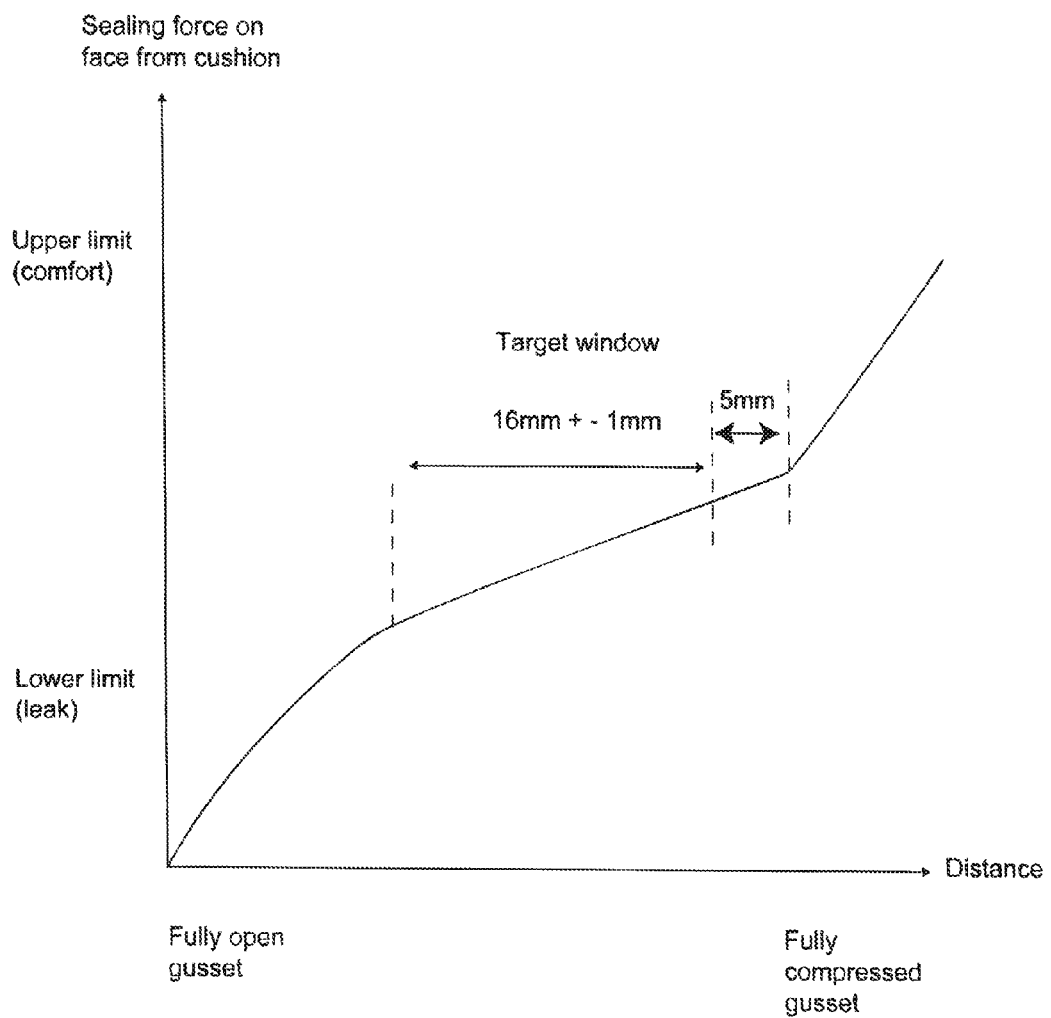
Figure 8:
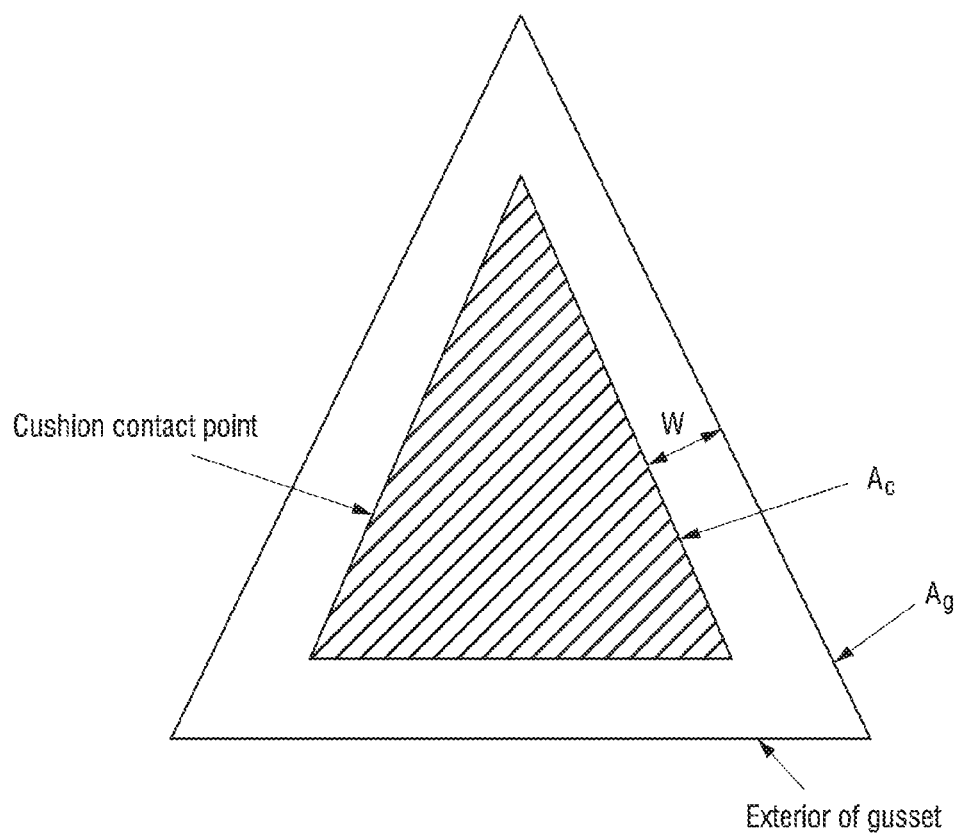

As is shown in FIG. 6 and the cross-sections thereof depicted in FIGS. 6-1 to 6-8, the gusset 16B in accordance with this further embodiment of the present invention has a minimal widthwise dimension around the upper (nasal bridge) region 16B-1, and a substantially constant maximum width along the lower region 16B-2 which extends substantially from one cheek bone area of the patient to the other. Substantially linear (straight) side regions 16B-3 from generally the nasal bridge area to each cheek bone area of the patient provide widthwise transition sections from the minimal width thereof at upper region 16B-1 to the maximum width thereof at lower region 16B-2. Most preferably, the upper region 16B-1 occupies between about 15% to about 30% of the cushion's perimeter distance, and lower region 16B-2 occupies between about 50% to about 70% of the cushion's perimeter distance, with side regions 16B-3 occupying the remainder perimeter distance.

The projected area of the gusset 16B, $A_g$, is preferably between about 80 cm² to about 140 cm², more preferably approximately 130 cm², as measured in its natural molded state (i.e., uncompressed). Of course, the area could be higher or lower, depending on application. In this regard, since little additional sealing force is required in the nasal bridge region, the upper gusset region 16B-1 does not necessarily require any projected area, hence the zero or near zero width in that region. Moreover, the substantially straight side regions impart structural stability to the gusset 16B in the upper region 16B-1. Also, the gusset 16B in the nasal bridge region has a generally w-shaped cross-sectional configuration (see FIG. 6-1) which may provide spring-like characteristics in use.

It will be observed in the cross-sections of FIGS. 6-1 to 6-8 that the gusset 16B has the same travel distance towards and away from the patient's face due to the fact that the gusset 16B has the same effective dimension in the travel direction at any perimetrical location. However, at different perimetrical locations, the exterior and interior lateral projections thereof will vary so as to achieve the minimal width dimension along the upper region 16B-1 (see FIG. 6-1), and the maximum width dimensions along the lower region 16B-2 (see FIGS. 6-5 to 6-8). Widthwise transitions will however be present along the side regions 16B-3 (see FIGS. 6-2 to 6-4).

FIG. 7 is a plot of sealing force (Kg) on a patient's face due to contact with cushions in accordance with the present invention versus displacement distance of the mask frame towards the patient's face (i.e., from a fully expanded (open) travel state of the gusset to a fully compressed state (closed) travel state of the gusset. As is seen, the target travel window of 16 mm (+/−1 mm) achieved by the gussets of the present invention dramatically flatten the pressure curve so as to maintain comfort for the patient and reduce the importance of a particular strap length setting on sealing performance.

Figure 9A:
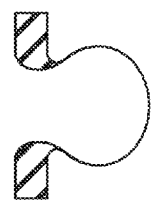
FIGS. 9A-9Y are partial schematic views according to further cushion embodiments of the present invention.
Figure 9B:
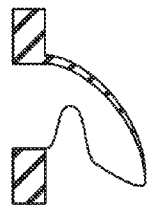
Figure 9C:
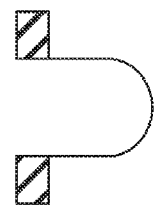
Figure 9D:
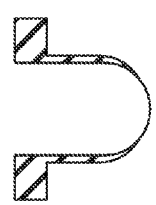
Figure 9E:
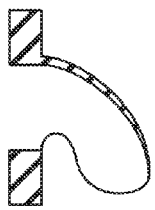
Figure 9F:
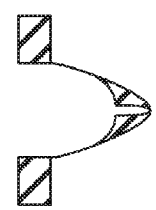
Figure 9G:
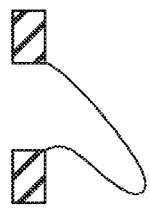
Figure 9H:
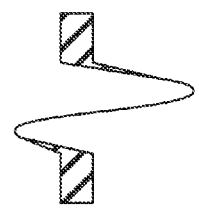
Figure 9I:
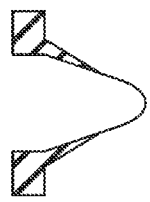
Figure 9J:
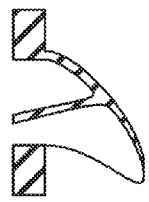
Figure 9K:
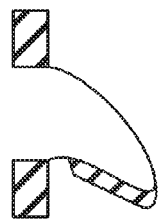
Figure 9L:
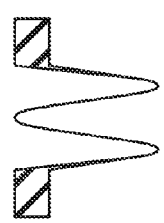
Figure 9M:
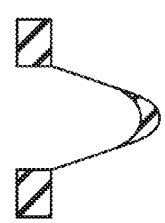
Figure 9N:
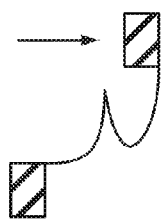
Figure 9O:
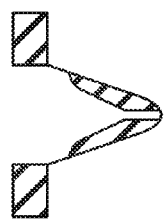
Figure 9P:
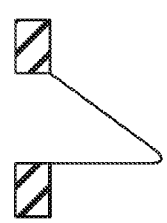
Figure 9Q:
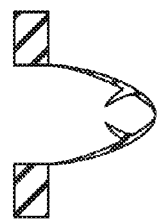
Figure 9R:
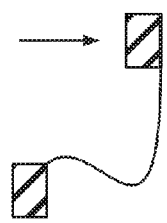
Figure 9S:
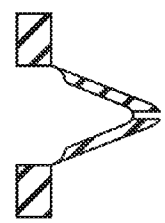
Figure 9T:
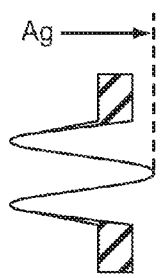
Figure 9U:
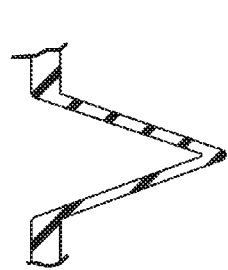
Figure 9V:
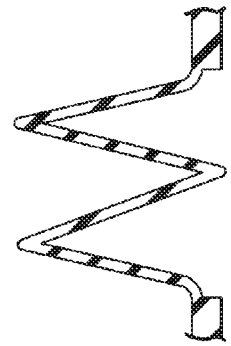
Figure 9W:
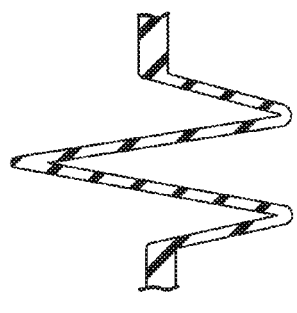
Figure 9X:
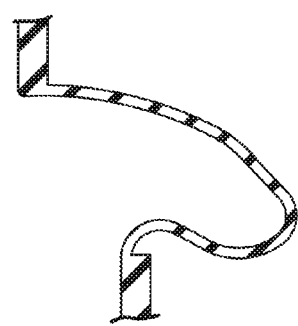
Figure 9Y:
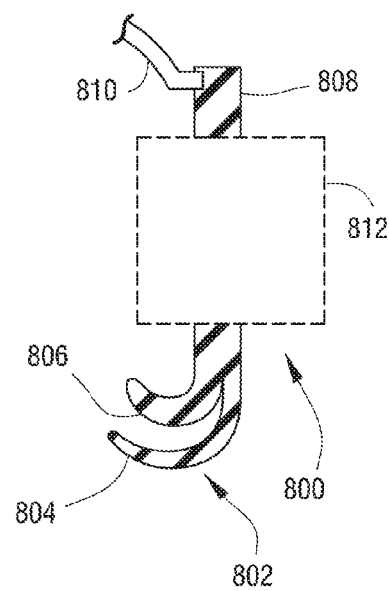

FIGS. 9A-9Y illustrate further embodiments according to the present invention. FIG. 9Y schematically illustrates a partial section of a mask assembly 800 having a cushion including a face contacting/interacting portion 802 that may include a membrane 804 with an optional underlying rim 806. Cushion includes a non-face contacting portion 808 that is supported by a frame 810. A central portion 812, in the form of a black box, is provided between portions 806 and 808.

FIGS. 9A-9X illustrate various central portions that can be used for control portion 812 in FIG. 9Y. In the case of FIGS. 9N and 9R, face-contacting interacting portion 808 and/or frame 810 (FIG. 9Y) would be adjusted, e.g., widened, to accommodate for illustrated offset. Various features of FIGS. 9A-9X are tabulated below in Table 1.

TABLE 1

| Drawings | Comment |
|---|---|
| FIG. 9A | Circular cross-section. Provides more travel for the same outer area. The circular shape will deform less when pressurized, therefore outer area remains constant. |
| FIG. 9B | Underside notch has dual purpose. On extension provides more travel (longer path length), on compression acts as spring. Upperside is tapered wall section. |
| FIG. 9C | Circular cross-section at end of straight gusset. Provides more travel for the same outer area. The circular shape will deform less when pressurized, therefore outer area remains constant. |
| FIG. 9D | Like FIG. 9C, but with tapered or thickened wall section. When pressurized, the thickened wall section tends to keep the form. |
| FIG. 9E | Underside notch provides more travel on extension. This is assisted by the thickened upper wall which tends to keep the form. This also allows for a constant outer area ($A_g$). |
| FIG. 9F | In compression, a spring constant is added. In extension, no spring effect (one-sided spring). This has the advantage of having a spring at low pressures but not necessarily at high pressures. |
| FIG. 9G | Angled gusset provides more travel for the same outer area. |
| FIG. 9H | Internal gusset provides more travel for the same outer area. |
| FIG. 9I | Thickened section deforms only under higher pressures. At lower pressures, thickened section will touch when gusset is compressed and act as spring. This has the advantage of having a spring at low pressures but not necessarily at high pressures. |
| FIG. 9J | Thickened section deforms only under higher pressures. This moves the spring tab away from the lower section (i.e., no spring). At lower pressures, spring tab will touch when gusset is compressed and act at spring. This has the advantage of having a spring at low pressures but not necessarily at high pressures. |
| FIG. 9K | Thickened section will not deform under pressure, maximizes outer area with respect to FIG. 9G. Angled gusset also provides for more travel for the same area. |
| FIG. 9L | Double gusset provides more travel for the same outer area. |
| FIG. 9M | Spring element added. |
| FIG. 9N | Attachment point moved outwards. Outer area maintained fixed. Underside notch provides more travel (longer path length). |
| FIG. 9O | In compression, a spring constant is added. In extension, no spring effect (one-sided spring). Note: Similar to but more spring and less expansion of the gusset at high pressures. |

TABLE 1-continued

| Drawings | Comment |
| --- | --- |
| FIG. 9P | Angled gusset provides more travel for the same outer area. |
| FIG. 9Q | In compression, a spring constant is added. In extension, no spring effect (one-sided spring). Similar to FIG. 9F, this has the advantage of having a spring at low pressures but not necessarily at high pressures. |
| FIG. 9R | Attachment point moved outwards. Outer area maintained fixed. Shape of gusset provides more travel (longer path length). |
| FIG. 9S | Spring effect in extension. No spring effect in compression. Thick walls provide more constant outer area under pressure. |
| FIG. 9T | Double internal gusset allows for outer area to be varied from large to none while still allowing significant travel. |
| FIG. 9U | This cushion cross-section represents a direct translation of the geometry of the gusset of the Activa ™ nasal mask onto a full face platform. |
| FIG. 9V | Gusset may be provided around entire perimeter of full face cushion. The everted gusset does not protrude past the footprint of the cushion. |
| FIG. 9W | Starting with the cushion of FIG. 9U, an inverted gusset has been added to produce two smaller everted gussets. |
| FIG. 9X | A hanging gusset is provided around entire perimeter of full face cushion. Gusset molded from an open-shut tool. |

Notes:
1 Extension is taken to be movement of frame away from lower cushion
2 Compression is taken to be movement of frame towards lower cushion
3 Travel is taken to be amount of extension plus compression
4 Outer area is taken to be the outer area of the gusset While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A respiratory mask assembly for treatment of sleep disordered breathing, the respiratory mask assembly comprising:
a frame;
a cushion which at least in part defines a cavity adapted to receive at least a patient's nose,
wherein the cushion includes:
a face contacting portion,
a non-face contacting portion, and
a gusset portion between the face contacting portion and the non-face contacting portion,
wherein, when seen in cross-section:
the gusset portion includes a hanging portion that hangs over an adjacent exterior surface of the cushion, and
the gusset portion includes a first end adjacent to the face contacting portion and a second end adjacent to the non-face contacting portion, and the first end is offset radially outwardly from the second end,
wherein the gusset portion includes only a single gusset,
wherein the single gusset includes a first gusset wall that joins the face contacting portion at the first end, a second gusset wall that joins the non-face contacting portion at the second end, and a tip section that interconnects the first gusset wall and the second gusset wall,
wherein the tip section is positioned radially outwardly with respect to the non-face contacting portion,
wherein the tip section is offset radially outwardly from the first end and the second end, and
wherein a radial offset between the tip section and first end is greater than a radial offset between the first end and the second end; and
an air delivery connection supported by the frame and adapted to connect an air delivery conduit to supply air to the cavity.

2. The respiratory mask assembly according to claim 1, wherein the gusset portion includes a thickness in cross-section that is substantially uniform along its entire length.

3. The respiratory mask assembly according to claim 1, wherein the face contacting portion includes a side wall and a membrane extending from the side wall.

4. The respiratory mask assembly according to claim 1, further comprising a reinforcing member provided to a side wall of the face contacting portion.

5. The respiratory mask assembly according to claim 4, wherein the reinforcing member is provided at a nasal bridge region of the cushion.

6. The respiratory mask assembly according to claim 5, wherein the reinforcing member extends from one side, over an apex, and then to the other side of the nasal bridge region.

7. The respiratory mask assembly according to claim 6, wherein the reinforcing member is narrower near the apex.

8. The respiratory mask assembly according to claim 1, wherein the gusset portion includes an outer wall configured to fold over and outside of an inner wall of the gusset portion when the face contacting and non-face contacting portions are compressed towards one another.

9. The respiratory mask assembly according to claim 1, wherein the cushion includes an increased cross-sectional thickness in a region of the non-face contacting portion near the gusset portion.

10. The respiratory mask assembly according to claim 1, wherein the gusset portion includes a constant projected outer area under extension and compression.

11. The respiratory mask assembly according to claim 1, wherein the respiratory mask assembly is adapted to supply air at least to a patient's nose.

12. The respiratory mask assembly according to claim 11, wherein the respiratory mask assembly is adapted to supply air to a patient's mouth.

13. The respiratory mask assembly according to claim 1, wherein a thickness of the gusset portion is thinner in cross-section than a thickness of the non-face contacting portion.

14. The respiratory mask assembly according to claim 1, further comprising a forehead support assembly.

15. The respiratory mask assembly according to claim 1, wherein the frame comprises headgear connectors for a headgear assembly.

16. The respiratory mask assembly according to claim 1, further comprising a headgear assembly.

17. The respiratory mask assembly according to claim 1, wherein the gusset portion is configured and arranged to protrude laterally outwardly with respect to the non-face contacting portion.

18. The respiratory mask assembly according to claim 1, wherein the first end is further from a center of the cushion than the second end.

19. The respiratory mask assembly according to claim 1, wherein an apex of the tip section is positioned radially outwardly with respect to the non-face contacting portion.

20. The respiratory mask assembly according to claim 1, wherein the face contacting portion includes a side wall and a membrane extending from the side wall, and further comprising a reinforcing member provided to the side wall to provide reinforcement to the side wall, wherein the single gusset and the reinforcing member are provided at a nasal bridge region of the cushion.

21. The respiratory mask assembly according to claim 1, further comprising a reinforcing member provided to a side wall of the face contacting portion to provide reinforcement to the side wall, wherein the reinforcing member is arranged between the single gusset and the face contacting portion.

22. The respiratory mask assembly according to claim 1, wherein the face contacting portion includes a membrane and an underlying rim.

23. The respiratory mask assembly according to claim 22, wherein the underlying rim is radially outwardly from the second end.

* * * * *